United States Patent [19]

Yamaguchi et al.

[11] Patent Number: 5,156,728

[45] Date of Patent: Oct. 20, 1992

[54] ION SENSOR

[75] Inventors: Shuichiro Yamaguchi; Takanao Suzuki; Takeshi Shimomura, all of Fuji; Noboru Oyama, Fuchu, all of Japan

[73] Assignee: Terumo Kabushiki Kaisha, Tokyo, Japan

[21] Appl. No.: 751,581

[22] PCT Filed: Feb. 12, 1988

[86] PCT No.: PCT/JP88/00143

§ 371 Date: Oct. 10, 1989

§ 102(e) Date: Oct. 10, 1989

[87] PCT Pub. No.: WO88/06289

PCT Pub. Date: Aug. 25, 1988

Related U.S. Application Data

[63] Continuation of Ser. No. 415,331, filed as PCT/JP88/00143, Feb. 12, 1988.

[30] Foreign Application Priority Data

Feb. 12, 1987 [JP] Japan ............... 62-028330

[51] Int. Cl.⁵ .......................................... G01N 27/30
[52] U.S. Cl. .................................. 204/416; 204/418
[58] Field of Search ............... 204/416, 418; 427/122

[56] References Cited

U.S. PATENT DOCUMENTS

| | | | |
|---|---|---|---|
| 2,016,139 | 10/1935 | Eddison | 427/122 X |
| 2,057,124 | 10/1936 | Van Gessel et al. | 427/122 X |
| 4,225,410 | 9/1980 | Pace | 204/412 |
| 4,454,007 | 6/1984 | Pace | 204/418 X |
| 4,528,085 | 7/1985 | Kitajima et al. | 204/416 |
| 4,615,954 | 10/1986 | Solomon | 429/27 |
| 4,683,048 | 7/1987 | Yamada et al. | 204/416 |
| 4,705,646 | 11/1987 | DuPont et al. | 427/122 X |
| 4,753,719 | 6/1988 | Yamaguchi et al. | 204/418 |
| 4,798,664 | 1/1989 | Yamaguchi et al. | 204/418 |
| 4,816,118 | 3/1989 | Oyama et al. | 204/418 |
| 4,839,020 | 6/1989 | Yamaguchi et al. | 204/431 |
| 4,861,454 | 8/1989 | Ushizawa et al. | 204/414 |

FOREIGN PATENT DOCUMENTS

| | | |
|---|---|---|
| 208081 | 5/1956 | Australia . |
| 0056283 | 7/1982 | European Pat. Off. . |
| 0186210 | 7/1986 | European Pat. Off. . |
| 228969 | 7/1987 | European Pat. Off. . |
| 118153 | 7/1982 | Japan . |
| 58-200157 | 11/1983 | Japan . |
| 251764 | 11/1986 | Japan . |
| 21055 | 1/1987 | Japan . |
| 1209019 | 10/1970 | United Kingdom . |

OTHER PUBLICATIONS

Snell et al., "Surface Modified Electrodes", Chem. Soc. Rev. 1979, 8, 259-282.

Primary Examiner—John Niebling
Assistant Examiner—Arun S. Phasge
Attorney, Agent, or Firm—Burns, Doane, Swecker & Mathis

[57] ABSTRACT

A portion of a board (1) on which copper wiring is printed is provided with a carbon coating, the board (1) and lead wires (2) are joined by solder (3), the portion having the solder (3) is insulated with a silicone resin (4), and the carbon-coated printed wiring portion (10a) is successively coated with a redox layer (11) obtained by electro-oxidation of 2,6 xylenol and an ion-selective layer (12), thereby forming an ion sensor (20).

Since the ion sensor can be formed on a printed wiring board, various devices which include an ion sensor can readily be fabricated on a board.

5 Claims, 4 Drawing Sheets

ION SENSOR

This application is a continuation of application Ser. No. 415,331, filed as PCT/JP88/00143, Feb. 12, 1988.

TECHNICAL FIELD

This invention relates to an ion sensor and, more particularly, to an ion sensor that uses a board on which an ion-sensitive portion is formed.

BACKGROUND ART

The inventors have filed applications for ion sensors employing a carbon electrode (in which basal plane pyrolytic graphite carbon, namely BPG carbon, glassy carbon or the like is used as the electrically conductive carbon material) as a substrate, wherein the board is coated with a redox layer which may in turn be coated with an ion-selective layer.

With ion sensors so configured, however, there is a limitation upon the shape of the board and difficulties are encountered particularly in miniaturization and in utilizing the above-described art in circuit techniques involving semiconductors and the like.

In the future, sensor techniques employing ion sensors will not be limited to systems in which mere measurements are taken by using a sensor. Since there will be a need to develop software in the electronic, electrical, biological and fermentation fields and in the field of medicine (clinical medicine, diagnosis, examination, communication, etc.), it will be required to develop sensor technology in combination with sophisticated board technology.

DISCLOSURE OF THE INVENTION

The present invention provides an ion sensor using a board on which an ion-sensitive portion is formed and which is utilizable in circuit board technology as well.

As means for solving this problem, the ion sensor of the present invention is equipped with a board on which an ion-sensitive portion is formed, a carbon layer which includes carbon coating the ion-sensitive portion, and a redox layer coating the carbon layer and exhibiting a redox function.

In this arrangement, an electric potential which corresponds to an ion concentration is produced in the ion-sensitive portion formed on the board.

In accordance with the present invention, there can be provided an ion sensor using a board on which an ion-sensitive portion is formed and which is utilizable in circuit board technology as well.

More specifically, in accordance with the present invention, (1) ultrafine wiring can be coated with electrically conductive carbon in a simple manner, and it is possible to form the carbon board constructed of insulated wiring;

(2) the carbon board can be coated with a pin hole-free redox responsive membrane by an electrooxidative reaction; and (3) the ion sensor is of a composite membrane-type coated with an ion-selective membrane.

Since a printed circuit board, namely a screen-printed board or a semiconductor circuit board, can readily be coated with the abovementioned membranes, this technique can be utilized in fields that apply this sensor technology, e.g., in the electronic, electrical, biological and fermentation fields and in the field of medicine (clinical medicine, diagnosis, examination, communication, etc.).

BEST MODE FOR CARRYING OUT THE INVENTION

Embodiments of the present invention will now be described in detail in accordance with the accompanying drawings.

EXAMPLE 1

Figure 1:
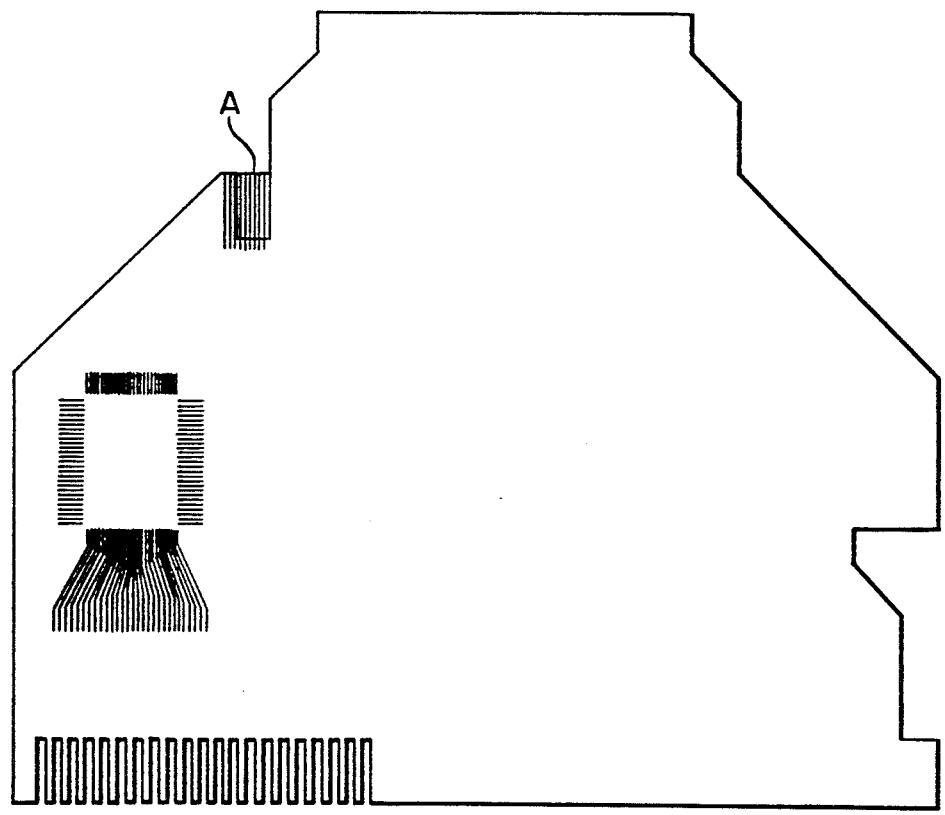
FIG. 1 is a prototypal view of a printed board used in a first embodiment.

(1) As shown in FIG. 1, a board 1 was fabricated by applying, by means of a brush, a single layer (membrane thickness: about 0.5 mm) of a carbon paste (viscosity: 150–300$p_s$; JEF-010, manufactured by Nihon Achison K. K.) to a portion A of a board (having a wire width of 0.1 mm at fine portions, manufactured by Mitsui Kinzoku Kogyo K. K.) obtained by printing copper wiring on a polyimide film, and sintering the board for 30 min at a sintering temperature of 150° C. "JEF-010" (graphite) is a high quality electrically conductive ink primarily used for screen printing. This material is characterized as follows:

Features:

1. Semi flexible-type conductive ink which enables printing circuit patterns with its excellent electrical characteristics;

2. Scratching durability and wear resistance with minute particles of graphite being dispersed in a thermosetting binder;

3. Suitability for application to rigid substrate printing, contract printing or circuit printing of separate membrane;

4. Solvent proof;

5. Moisture proof (70° C., 95% RH-240 hours);

6. Heat proof (max 200° C.);

Typical uses

1. Circuit printing of separate membrane;
2. Contact printing;
3. Potentiometer printing;
4. Terminal printing;
5. Keyboard Switch;

Specifications—Characteristics of Liquid

Figure 2A:
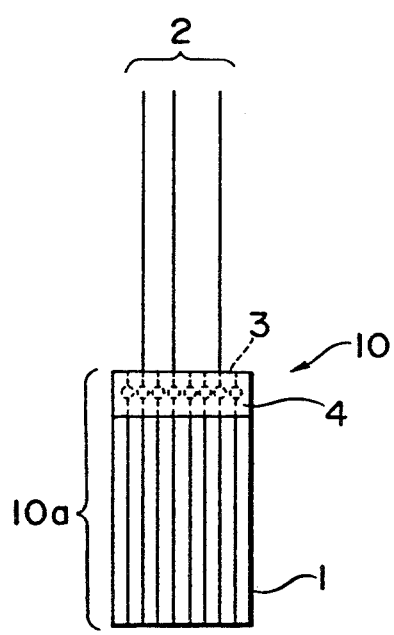
FIG. 2(a) shows an electrically conductive carbon electrode of the first embodiment.
Figure 2B:
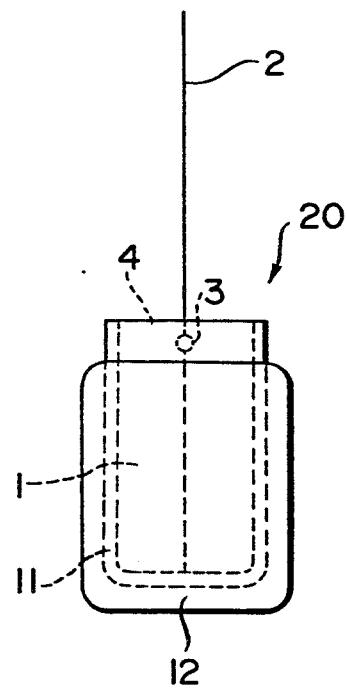
FIG. 2(b) shows a film board electrode of the first embodiment.

1. Electrically conductive particle: graphite
2. Binder: thermosetting resin;
3. Viscosity: 15,000–30,000 cps;
4. Density: 1.21 kg/l;
5. Effective period of storage: about 6 months under seal. Next, an electrically conductive carbon electrode 10 shown in FIG. 2(a) was fabricated by joining the board 1 and urethane-coated copper wires 2 (lead wires) using solder 3, and insulating the soldered portion 3 with a silicone resin 4.

(2) A film board electrode 20 was fabricated by carrying out an electro-oxidative reaction under the conditions given below to coat a carbon-coated printed wiring portion 10a of the electrically conductive electrode 10, which was fabricated in accordance with method (1), with a redox layer 11, and coating the resulting element with a hydrogen ion carrier membrane 12.

With regard to the electro-oxidative reaction conditions, use was made of a three-pole cell in which the abovementioned electrically conductive carbon electrode 10 was employed as a working electrode, an SSCE as a reference electrode, and a platinum mesh as a counter electrode.

Electro-oxidative reaction conditions

Electrolyte: 0.5M 2,6 xylenol, 0.2M sodium perchlorate acetonitrile solvent
Electrolytic temperature: −20.0° C.
Electrolytic conditions: After the electrolytic potential was swept twice from 0V to 1.5 V (vs. a saturated sodium calomel electrode) at a scan rate of 50 mV/sec, constant potential electrolysis was performed at 1.5 V for 10 min.

Next, a proton carrier membrane serving as the hydrogen ion carrier membrane 12 was formed on the electrode surface by dipping under the following conditions:

Proton carrier membrane composition

| TDDA | 313 mg | 6 wt % |
|---|---|---|
| KTpClPB | 31.3 mg | 0.6 wt % |
| DOS | 3255 mg | 62.3 wt % |
| PVC | 1625 mg | 31.1 wt % |
| THF solution | | |

Experiment 1

Figure 4:
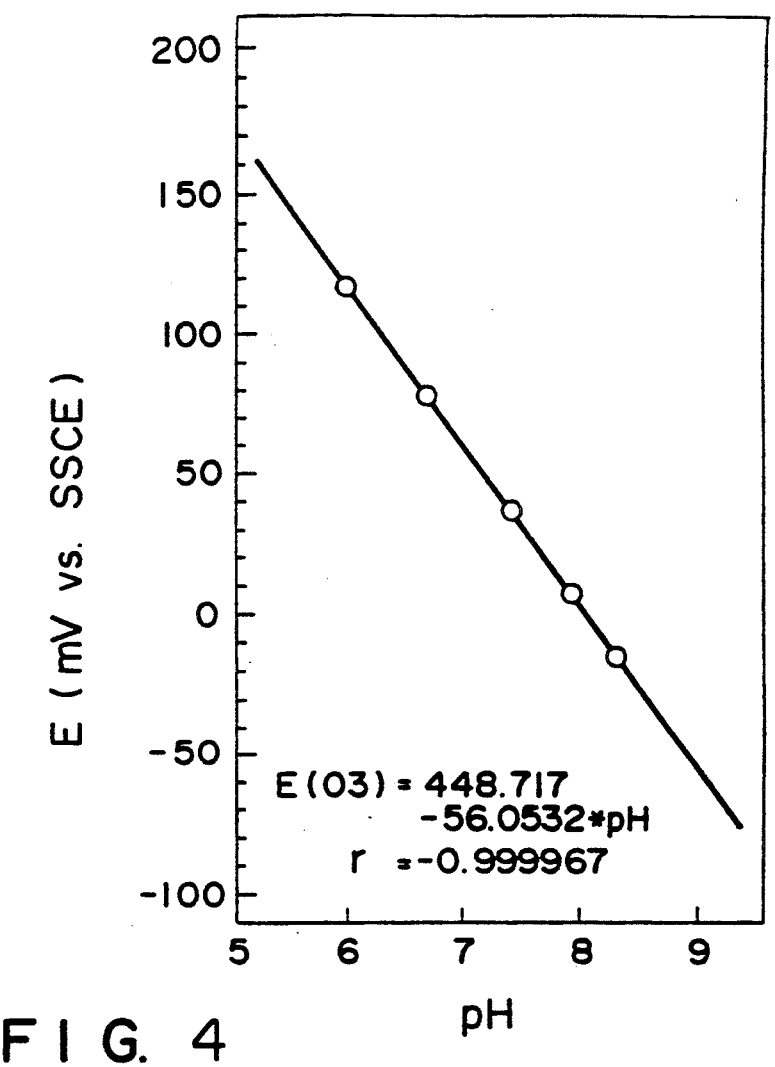
FIG. 4 is a view showing experimental results in the first embodiment.
Figure 3:
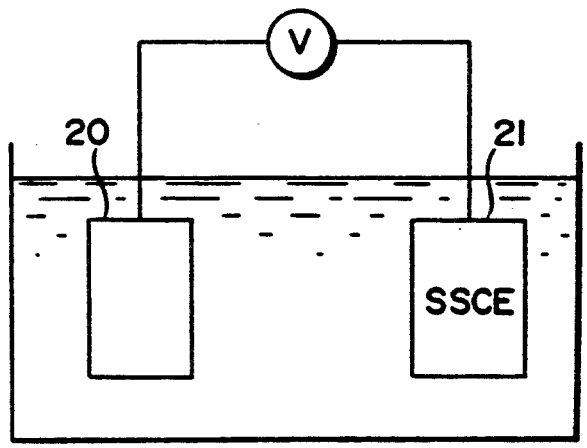
FIG. 3 is a view showing a circuit for measuring emf response in the first embodiment.

When the relationship between pH and the emf response of the film board electrode 20 was measured over a pH range of 5-9 in a standard buffer solution by the circuit shown in FIG. 4 using the film board electrode 20, which was prepared as described above, and an SSCE electrode 21, the results obtained showed a linear relationship, as illustrated in FIG. 3, with the slope of the straight line being 56.05 mV/pH (37° C.).

Thus, there was fabricated a sensor having a high possibility of practical use as a sensor capable of pH measurement with a printed wiring film (thin membrane).

EXAMPLE 2

Figure 5:
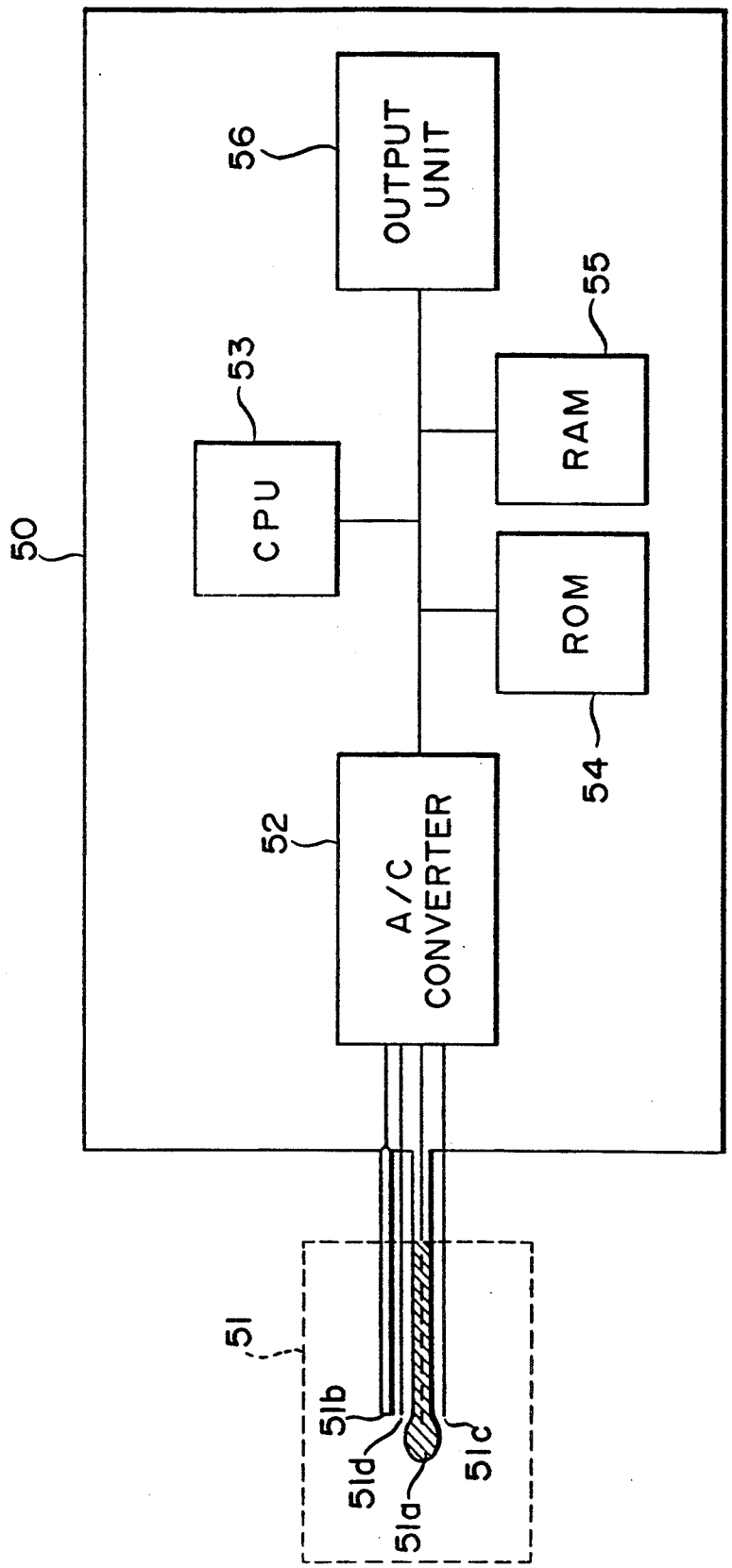
FIG. 5 is a structural view showing a handy ion sensor of a second embodiment.

A handy-type ion sensor 50 is shown in FIG. 5.

The ion sensor 50 receives an input of various analog data from a sensor input unit 51 comprising an ion sensor electrode 51a, a reference electrode 51b, a common electrode 51c and a thermister 51d. These data are converted into digital data by an A/D converter 52. On the basis of these data and in accordance with a program stored in a ROM 54, a CPU 53 computes an ion concentration and outputs the same to an output unit 56 while storing data in a RAM 55.

Though a handy-type ion sensor has been described as one example, various devices which include an ion sensor can readily be fabricated on a board by the technical concept of the present invention, and an apparatus capable of measuring a plurality of ion types simultaneously can be obtained. Furthermore, the invention paves the way for application to integrated circuitry and to devices in which integrated circuits are coated with ion-selective layers.

Though a hydrogen ion carrier membrane is described as typifying the ion carrier membrane in the present embodiment, similar results can also be obtained in other ion carrier membranes for anions such as calcium ion, potassium ion, sodium ion, magnesium ion and ammonium ion, as well as for carbon ion, chlorine ion, phosphate ion, acetate ion and sulphuric acid ion. The same is true for gas sensors for oxygen, carbon dioxide gas and the like, and for biosensors such as enzyme sensors.

Though carbon paste was used as the carbon material in the embodiments, it is also permissible to use a carbon-containing toner, a carbon-containing emulsion or a carbon-containing electrically conductive adhesive.

What is claimed is:

1. An ion sensor comprising:
   a printed board on which a plurality of conductive wires about 0.1 mm in width are closely printed;
   a plurality of sintered carbon layers each formed on one of said conductive wires, said sintered carbon layers being made by applying and sintering a carbon-containing paste including carbon particles in thermosetting resin binder; and
   a plurality of redox layer made by an electrolytic oxidative polymerization process each coating one of the sintered carbon layers and exhibiting a redox function.

2. An ion sensor according to claim 1, further comprising a plurality of ion-selective layers each coating one of said redox layers and exhibiting ion selectivity.

3. An ion sensor according to claim 2, wherein each of at least two different kinds of said ion-selective layers is formed on a different conductive wire.

4. An ion sensor comprising:
   a printed board on which a plurality of conductive wires about 0.1 mm in width are closely printed;
   a sintered carbon layer formed on one of said conductive wires, said sintered carbon layer being made by applying and sintering a carbon-containing paste including carbon particles in thermosetting resin binder;
   a redox layer made by an electrolytic oxidative polymerization process coating said sintered carbon layer and exhibiting a redox function; and
   a reference electrode, a common electrode, a thermistor or a combination thereof formed on said conductive wires adjacent to said one of conductive wires on which said sintered carbon layer and redox layer are formed.

5. An ion sensor according to claim 4, further comprising a ion-selective layer coating said redox layer and exhibiting ion selectivity.

* * * * *

UNITED STATES PATENT AND TRADEMARK OFFICE
CERTIFICATE OF CORRECTION

PATENT NO. : 5,156,728

DATED : October 20, 1992

INVENTOR(S) : Shuichiro YAMAGUCHI et al

It is certified that error appears in the above-identified patent and that said Letters Patent is hereby corrected as shown below:

In Column 3, line 58, delete "A/D" and insert -- A/C --.

Signed and Sealed this

Twenty-sixth Day of October, 1993

*Attest:*

BRUCE LEHMAN

*Attesting Officer*   *Commissioner of Patents and Trademarks*